(12) United States Patent
Pomares Marco et al.

(10) Patent No.: US 12,312,315 B2
(45) Date of Patent: May 27, 2025

(54) PROCESS FOR THE PREPARATION OF ARIPIPRAZOLE LAUROXIL

(71) Applicant: INTERQUIM, S.A., Sant Cugat del Vallès (ES)

(72) Inventors: Marta Pomares Marco, Sant Cugat del Vallès (ES); Francisco de Asís Marquillas Olondriz, Sant Cugat del Vallès (ES)

(73) Assignee: INTERQUIM, S.A., Barcelona (ES)

( * ) Notice: Subject to any disclaimer, the term of this patent is extended or adjusted under 35 U.S.C. 154(b) by 738 days.

(21) Appl. No.: 17/617,702

(22) PCT Filed: Jul. 10, 2020

(86) PCT No.: PCT/EP2020/069680
§ 371 (c)(1),
(2) Date: Dec. 9, 2021

(87) PCT Pub. No.: WO2021/009087
PCT Pub. Date: Jan. 21, 2021

(65) Prior Publication Data
US 2022/0242825 A1    Aug. 4, 2022

(30) Foreign Application Priority Data
Jul. 12, 2019   (EP) .................... 19382592

(51) Int. Cl.
*C07D 215/22*    (2006.01)
(52) U.S. Cl.
CPC ................. *C07D 215/22* (2013.01)
(58) Field of Classification Search
CPC .................................. C07D 215/22
See application file for complete search history.

(56) References Cited

U.S. PATENT DOCUMENTS

| | | | |
|---|---|---|---|
| 8,431,576 B2 | 4/2013 | Remenar et al. | |
| 9,452,131 B2 * | 9/2016 | Hickey | A61K 47/26 |
| 9,999,670 B2 * | 6/2018 | Perry | A61K 31/496 |
| 2018/0265472 A1 * | 9/2018 | Hsiao | C07D 215/22 |
| 2020/0140410 A1 * | 5/2020 | Pomares Marco | C07D 401/12 |

FOREIGN PATENT DOCUMENTS

WO    WO 2018/104953 A1    6/2018

OTHER PUBLICATIONS

International Search Report, issued in PCT/EP2020/069680, dated Aug. 10, 2020.
Written Opinion of the International Searching Authority, issued in PCT/EP2020/069680, dated Aug. 10, 2020.

* cited by examiner

*Primary Examiner* — D Margaret M Seaman
(74) *Attorney, Agent, or Firm* — Birch, Stewart, Kolasch & Birch, LLP

(57) ABSTRACT

It is provided a process for the preparation of aripiprazole lauroxil that comprises reacting 1-(hydroxymethyl) aripiprazole with lauric anhydride in the presence of DMAP and a solvent.

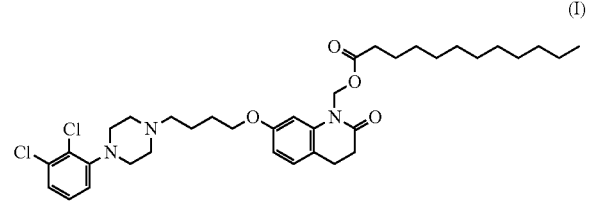

(I)

19 Claims, No Drawings

PROCESS FOR THE PREPARATION OF ARIPIPRAZOLE LAUROXIL

This application claims the benefit of European Patent Application EP19382592.4 filed Jul. 12, 2019.

TECHNICAL FIELD

The present invention relates to an improved process for the preparation of aripiprazole lauroxil.

BACKGROUND ART

Aripiprazole lauroxil is the generic name of compound 7-[4-[4-(2,3-dichlorophenyl)-1-piperazinyl]-butoxy]-2-oxo-3,4-dihydro-2H-quinolin-1yl)methyl dodecanoate, which chemical structure is:

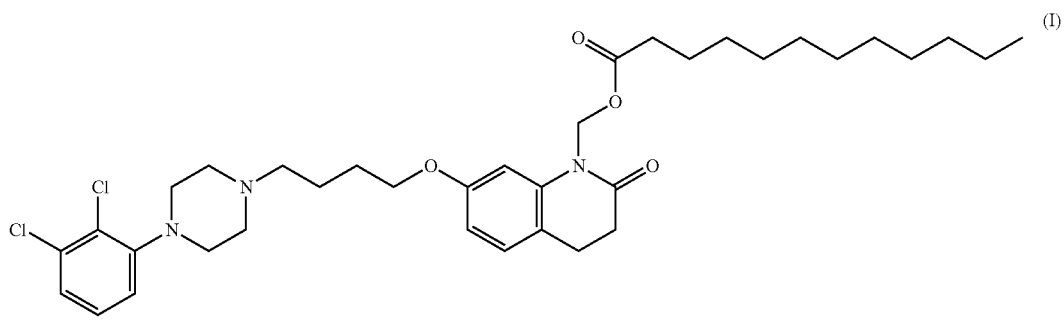 [SMILES: CCCCCCCCCCCC(=O)OCN1C(=O)CCc2ccc(OCCCCN3CCN(c4cccc(Cl)c4Cl)CC3)cc21]

(I)

Aripiprazole lauroxil is an atypical antipsychotic agent developed by Alkermes under the trade name Aristada® for the treatment of schizophernia.

7-{4-[4-(2,3-dichlorophenyl)-1-piperazinyl]butoxy}-2-oxo-3,4-dihydro-2H-quinolin-1-yl)methyl dodecanoate was first disclosed in U.S. Pat. No. 8,431,576.

U.S. Pat. No. 8,431,576 discloses a process for the preparation of aripiprazole lauroxil in two synthetic steps from aripiprazole with low yields and less purity.

Aripiprazole is reacted with formaldehyde in the presence of triethylamine and dimethylformamide to give 1-hydroxymethyl aripiprazole of formula (II). Conversion of aripiprazole to 1-hydroxymethyl aripiprazole in the presence of formaldehyde and triethyl amine, results 65% of 1-hydroxymethyl aripiprazole and 25% of aripiprazole. Then 1-hydroxymethyl aripiprazole of formula (II) is reacted with lauric anhydride in tetrahydrofuran in the presence of triethylamine to give the crude compound of formula (I), followed by purification using chromatography to obtain pure Aripiprazole lauroxil. The desired product was isolated in 21% yield as a crystalline solid. The overall yield form aripiprazole to aripiprazole lauroxil was 13.7%.

Scheme 1 Preparation of Aripiprazole lauroxil disclosed in U.S. Pat. No. 8,431,576.

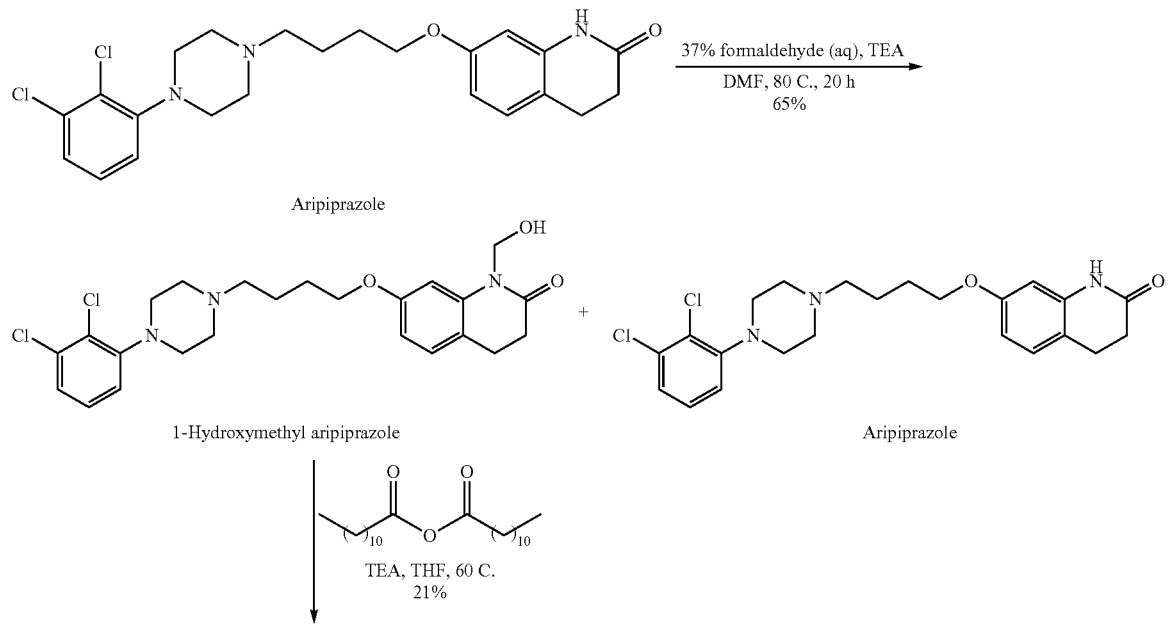

-continued

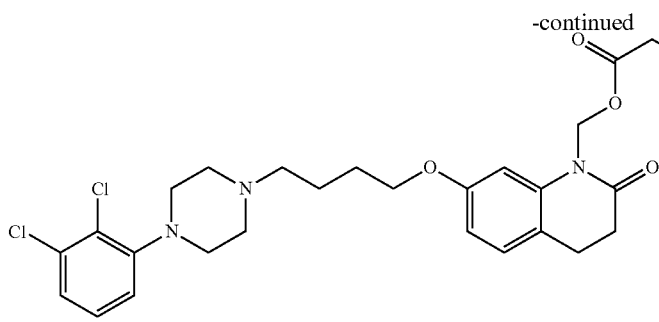

Aripiprazole lauroxil

The present inventors filed WO2019020821 which discloses an improved process of preparation of aripiprazole lauroxil. In step I, when compound of formula (II) is obtained in the absence of water by reacting aripiprazole with paraformaldehyde (instead of formaldehyde) conversion higher than 77% are obtained. In step II aripiprazole lauroxil is prepared by reacting 1-hydroxymethyl aripiprazole of formula (II) with lauric acid, N,N-dicyclohexylcarbodiimide, 4-dimethylaminopyridine in dichloromethane.

WO2018104953 and WO2018169491 also disclose, among other processes the preparation of aripiprazole lauroxil from 1-hydroxymethyl aripiprazole of formula (II) by reacting it with lauric acid in the presence of N,N-dicyclohexylcarbodiimide and 4-dimethylaminopyridine.

In the process mentioned above N,N-dicyclohexylurea which is a side-product in the reaction needs to be separated from the reaction mixture to isolate aripiprazole crude. Therefore, a filtration step is needed in the manufacturing process before removal of the solvent.

The solvent is then distilled at reduced pressure to isolate the reaction product. The present inventors have found that mixtures containing aripiprazole lauroxil and N,N-dicyclohexylurea are not stable when heated above 30° C. since the product decomposes to aripiprazole. Therefore, the solvent needs to be evaporated at room temperature and reduced pressure to avoid such degradation.

When a process is carried out at industrial scale and the solvent used is dichloromethane, distillation of the solvent at atmospheric pressure is always desirable to collect it completely and avoid solvent emissions to the atmosphere. On the other hand, sometimes it is desirable to crystallize the product from the reaction mixture by partial evaporation of the solvent to a certain amount to get an optimum crystallization yield. In an industrial process the calculation of the remaining solvent in the reaction mixture is performed by measuring the evaporated solvent. The evaporation of the solvent at atmospheric pressure ensures the total collection of the solvent, which allows to accurately measure the amount of solvent collected and consequentially the remainder in the reaction mixture. In the process mentioned above this is not possible.

In view of the above, there is still the need of finding new processes that allow preparing aripiprazole lauroxil in good yields and purity, easy to scale-up and which are environmentally friendly.

SUMMARY OF INVENTION

The present disclosure provides a new process for the preparation of aripiprazole lauroxil which works with good yields and purity, easy to industrialize and which avoids emission of toxic solvents to the atmosphere.

A first aspect of the invention refers to a process for the preparation of a compound of formula (I)

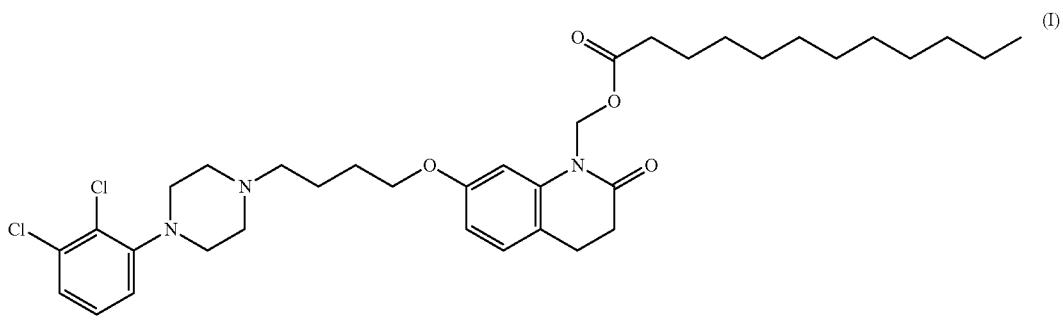 [SMILES: CCCCCCCCCCCC(=O)OCN1C(=O)CCc2ccc(OCCCCN3CCN(c4cccc(Cl)c4Cl)CC3)cc21]

which is aripiprazole lauroxil, which comprises the following steps:

a) reacting a compound of formula (II)

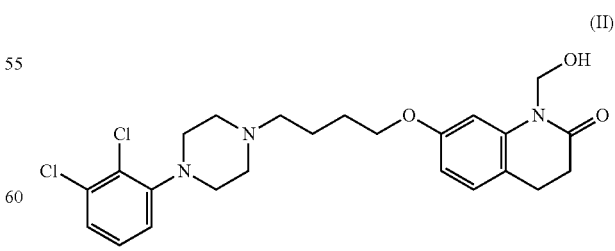

with lauric anhydride in the presence of DMAP and a solvent, to obtain aripiprazole lauroxil; and b) optionally isolating the obtained compound of formula (I).

The inventors have surprisingly observed that when compound of formula (I) is prepared by reacting compound of formula (II) with lauric anhydride in the presence of DMAP, instead of triethylamine, higher conversions are obtained compared with the processes described in U.S. Pat. No. 8,431,576. Particularly, in Example 12 of U.S. Pat. No. 8,431,576 the preparation of (7-(4-(4-(2,3-dichlorophenyl)piperazin-1-yl)butoxy)-2-oxo-3,4-dihydroquinolin-1(2H)-yl)methyl dodecanoate is carried out in an analogous fashion as described in Example 11 for the acetate analogue. The desired compound is obtained by reacting Compound-A1 in anhydrous tetrahydrofuran with lauric anhydride and heated for 2.0 hours at 60° C. (oil-bath). Then, triethylamine is added to the above solution, and stirred for 16 hours at 60° C. The product is isolated after work-up and purification by silica gel column chromatography. In Example 12 aripiprazole lauroxil was isolated as a crystalline solid with 21% yield. By following this example, the conversion of the compound of formula (II) into a compound of formula (I) is only of 26.7%, as shown in Comparative Example 2. Conversely, with the process of the present invention conversions higher than 85% are obtained, as can be seen in Examples 1 to 3 of the disclosure. The product can be isolated easily after solvent evaporation and crystallization in a suitable solvent.

Thus, surprisingly, inventors have found that the process of the invention allows obtaining aripiprazole lauroxil with good yields and at the same time with a high purity, as can be seen from the Examples and Comparative Example. The process is easy to scale-up to an industrial level; the product can be obtained after the end of reaction by simply evaporating the solvent and purifying it, for instance by crystallization. The process avoids any filtration step after the end of reaction.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

In the first aspect of the invention, the process of preparing aripiprazole lauroxil comprises a first step a) of reacting a compound of formula (II) with lauric anhydride in the presence of DMAP and a solvent.

Examples of solvents to carry out the reaction of compound of formula (II) with lauric acid include, without being limited to, toluene, dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof. Preferably the solvent is selected from toluene, tetrahydrofuran and dichloromethane. Particularly, the reaction is carried out in dichloromethane.

In a particular embodiment, optionally in combination with one or more features of the particular embodiments defined above or below, the solvent is selected form toluene, tetrahydrofuran and dichloromethane, and preferably is dichloromethane.

In another embodiment of the invention, the amount of DMAP used in the reaction between the compound of formula (II) and lauric anhydride can be from 0.1 to 1% molar respect to compound of formula (II). More particularly 0.2 to 0.3% molar respect to compound of formula (II).

In another embodiment of the invention, the molar ratio of compound of formula (II) to lauric anhydride can be from 1:1 to 1:3. More particularly the molar ratio is 1:1.3.

In another embodiment of the invention, the reaction temperature is in the range of 0° C. to the temperature of the boiling point of the solvent, still more particularly, at room temperature. For the purposes of the invention, room temperature is 15-25° C.

In the first aspect of the invention, the process of preparing aripiprazole lauroxil comprises a step b) of optionally isolating the product.

The product obtained in step a) can be isolated by conventional methods. The solvent can be directly removed to obtain aripiprazole lauroxil crude.

A filtration step to separate N,N-dicyclohexylurea form the reaction mixture is not needed before removal of the solvent in comparison to the process disclosed in the prior art when the reaction is carried out with lauric acid, DCC and 4-dimethylaminopyridine. The solvent can be removed by standard techniques used in organic chemistry as for example distillation. The solvent is preferably removed by distillation at atmospheric pressure. When a toxic solvent, as dichloromethane, is removed at atmospheric pressure, it has the advantage that the emission of volatiles to the atmosphere are reduced and they can be completely collected and recycled.

Thus, in a particular embodiment, optionally in combination with one or more features of the particular embodiments defined above or below, step b) is carried out by distilling the solvent at atmospheric pressure.

In another particular embodiment, optionally in combination with one or more features of the particular embodiments defined above or below, the solvent is dichloromethane and step b) is carried out by distilling the solvent at atmospheric pressure.

With the process of the invention aripiprazole lauroxil is obtained with high purity and very good yields. Particularly, aripiprazole lauroxil with a purity of at least 95% is obtained.

Additionally, the yield from compound of formula (II) to crude aripiprazole lauroxil range from 80% to 90%.

Aripiprazole lauroxil with a purity of at least 99.8% HPLC can be obtained by submitting the reaction crude to conventional purification techniques or other techniques described in the prior art such as crystallization, chromatography, or a combination thereof. Particularly, purification is carried out by crystallization, more particularly in isopropanol.

Previously, compound of formula (II) can be obtained by reacting aripiprazole of formula (III) or a hydrate thereof such as aripiprazole monohydrate with paraformaldehyde in the presence of an organic solvent and a suitable base, wherein the reaction is carried out either in the absence of water or in the presence of a content of water which comes from either the use of a non-anhydrous organic solvent, non-anhydrous reactants, or the use of a hydrated form of aripiprazole, without addition of further water, accordingly as described in WO2019020821.

Thus, in a particular embodiment, optionally in combination with one or more features of the particular embodiments defined above or below, the process of preparing aripiprazole lauroxil further comprises a previous step i) to prepare a compound of formula (II)

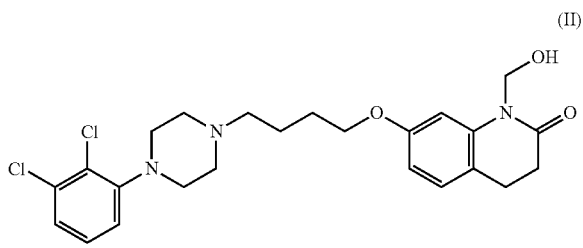 [SMILES: O=C1CCc2ccc(OCCCCN3CCN(c4cccc(Cl)c4Cl)CC3)cc2N1CO]

by reacting a compound of formula (III)

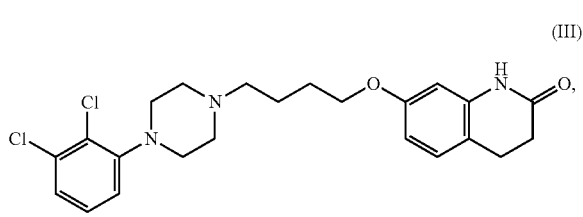 [SMILES: O=C1CCc2ccc(OCCCCN3CCN(c4cccc(Cl)c4Cl)CC3)cc2N1]

which is aripiprazole, or a hydrate thereof, with paraformaldehyde in the presence of an organic solvent and a suitable base, wherein the reaction is carried out either in the absence of water or in the presence of a content of water which comes from either the use of a non-anhydrous organic solvent, non-anhydrous reactants, or the use of a hydrated form of aripiprazole, without addition of further water.

Examples of organic solvents in step i) include, without being limited to, toluene, ethyl acetate, dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof. Particularly, the organic solvent is toluene.

Examples of bases include, without being limited to, 1,8-diazabicyclo[5.4.0]undec-7-ene, 1,4-diazabicyclo[2.2.2]octane, potassium carbonate, sodium carbonate, cesium carbonate, potassium tert-butoxide, and diisopropylethylamine. Particularly, the base is DBU.

In a particular embodiment, as mentioned above, the amount of water present in the reaction mixture comprising aripiprazole and paraformaldehyde is equal to or lower than 1 wt %.

The reaction can be carried out with a molar ratio of aripiprazole, or a hydrate thereof such as the monohydrate, to paraformaldehyde of from 1:1 to 1:3. More particularly the molar ratio is 1:1:1.7.

Aripiprazole used as the starting material as such or in form of a monohydrate, paraformaldehyde, and lauric anhydride are commercially available. Paraformaldehyde (CAS Number 30525-89-4), also known as polyoxymethylene, is a polymer of formaldehyde and can be represented by the chemical formula $(CH_2O)_n$, wherein n is an integer from 8 to 100.

Throughout the description and claims the word "comprise" and variations of the word, are not intended to exclude other technical features, additives, components, or steps. Furthermore, the word "comprise" encompasses the case of "consisting of".

The following examples are provided by way of illustration, and they are not intended to be limiting of the present invention. Furthermore, the present invention covers all possible combinations of particular and preferred embodiments described herein.

EXAMPLES

Example 1. Preparation of Compound of Formula (I) in Dichloromethane

Step 1: Preparation of 7-(4-(4-(2,3-dichlorophenyl)piperazin-1-yl)butoxy)-1-(hydroxymethyl)-3,4-dihydroquinolin-2(1H)-one (Compound of formula (II)) in toluene and 1,8-diazabicyclo[5.4.0]undec-7-ene (DBU)

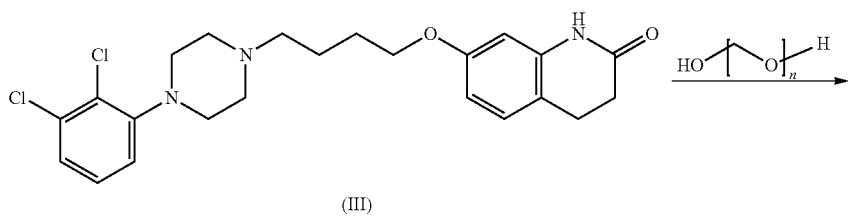

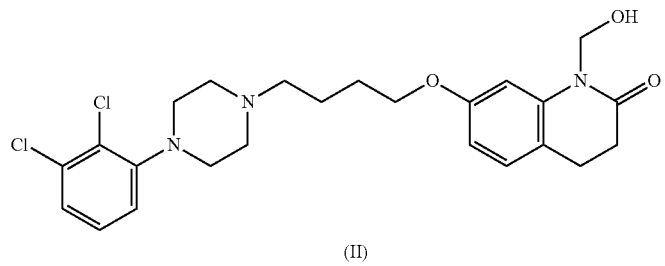

500 mL of toluene (5V), 100.0 g of aripiprazole (as monohydrate) (214 mmol), 10.6 g paraformaldehyde (343 mmol) and 0.65 g DBU (4.29 mmol) were charged into a 1 L reactor, heated to 30-40° C. and kept under stirring and nitrogen atmosphere during 16 hours (until aripiprazole in the reaction mixture is ≤16.0% HPLC).

The reaction mixture was cooled to T ≤ 5.0° C. and kept for 2 hours at these conditions. The solid was filtered from the mixture, washed once with 100 mL cool toluene. The solid was dried at 30° C. in a vacuum oven for 6 hours to obtain 96.9 g of the title compound (94% yield based on aripiprazole (as monohydrate)). Its purity, analyzed by HPLC was 87.6%, which means a conversion of 82.3%.

The HPLC analysis was carried out in the following column and conditions:
Chromatographic column: XBridge RP Shield C18 (150×3 mm, 3.5 μm);
Column temperature: 40° C.;

The solid is filtered from the reaction mixture, washed twice with 270 mL deionized water. The solid is dried at 30° C. in a vacuum oven for 16 hours. It is obtained 88.38 g of pure 7-(4-(4-(2,3-dichlorophenyl) piperazin-1-yl) butoxy)-1-(hydroxymethyl)-3,4-dihydroquinolin-2 (1H)-one (98.6% yield from crude).

Step 3: Preparation of aripiprazole lauroxil (compound of formula (I) in dichloromethane

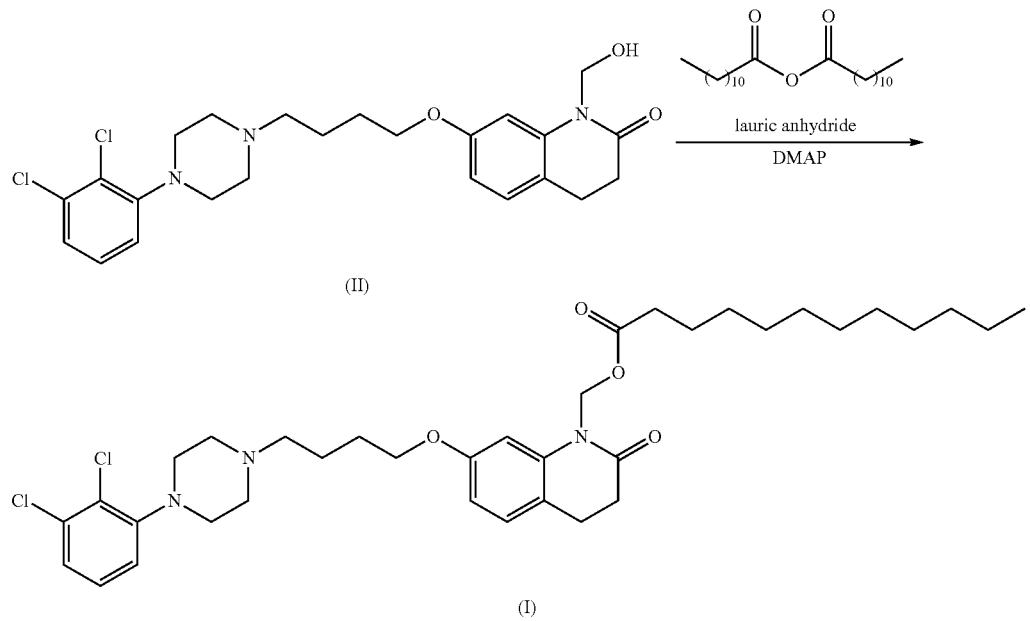

Mobile phase: A: 2.3 g K$_2$HPO$_4$+3H$_2$O/1 L H$_2$O pH=6.6 H$_3$PO$_4$ 10%,
  B: Acetonitrile
Gradient elution conditions:
The chromatograph was programmed as follows:

| Time (minutes) | Solution A (%) | Solution B (%) | Elution |
|---|---|---|---|
| 0 | 75 | 25 | Isocratic |
| 1.87 | 75 | 25 | Isocratic |
| 18.87 | 15 | 85 | Gradient |
| 22 | 15 | 85 | Isocratic |
| 22.5 | 75 | 25 | Return to initial |
| Post-time: 5 min | | | Re-equilibrate |

Main peak retention time: around 15.6 min; Sample volume 2 μL; Detection wavelength: 254 nm; running time: 22 min; Test solution: 1 mg/mL, Solvent: Acetonitrile: Milli-Q water at 10% AcOH (1:2); Column flow: 0.51 ml/min.

Step 2: Purification of Compound of Formula (II)

896 mL of deionized water (10V), 89.6 g of crude (7-(4-(4-(2,3-dichlorophenyl)piperazin-1-yl)butoxy)-1-(hydroxymethyl)-3,4-dihydroquinolin-2(1H)-one are charged into a 2 L reactor, heated to 18-28° C. and kept under stirring and nitrogen atmosphere during at least 30 minutes.

Dichloromethane 100 mL, 8.8 g of lauric anhydride (23.0 mmol), 10.0 g of compound of formula (II) obtained in step 1 or 2 (20.9 mmol) and 0.51 g 4-dimethylaminopyridine (4.18 mmol) were charged into a 250 mL reactor and kept under stirring at room temperature (15-25° C.) for a minimum of 2 hours (until compound of formula (II) in the reaction mixture was ≤0.5% HPLC). Results: 0% of unreacted starting material compound of formula (II), 11.24% of aripiprazole and 86.0% of aripiprazole lauroxil.

Dichloromethane was distilled at atmospheric pressure. 10 mL of solvent were left in the reaction mixture. Then, 140 mL of isopropanol were charged and 100 mL of solvent were distilled at reduced pressure. The reaction mixture was cooled to 0-10° C. It was kept 2 hour at 0-10° C. The mixture was filtered and the solid was washed twice with isopropanol (10 mL). The solid was dried under vacuum at 40° C. for 4 hours to obtain 12.4 g of aripiprazole lauroxil of 95.7% purity (analysed by HPLC).

Three recrystallizations were performed on aripiprazole lauroxil crude using isopropanol as solvent (200 mL). Finally, 10.4 g of aripiprazole (API quality) having a purity of 99.8% (analysed by HPLC) was obtained (75% overall yield from compound of formula (II)).

The HPLC analysis was carried out in the following column and conditions:
Chromatographic column: Gemini C6-phenyl C18 (150× 4.6 mm, 3.0 μm);
Column temperature: 40° C.;
Mobile phase: A: Acetonitrile B: Ammonium acetate pH=7.5

Gradient elution conditions:
The chromatograph was programmed as follows:

| Time (minutes) | Solution A (%) | Solution B (%) |
|---|---|---|
| 0 | 15 | 85 |
| 5 | 50 | 50 |
| 18 | 75 | 25 |
| 25 | 90 | 10 |
| 35 | 90 | 10 |
| 35.5 | 15 | 85 |
| Post-time: 5 min | | |

Main peak retention time: around 26.7 min; Sample volume 5 μL; Detection wavelength: 215 nm; running time: 35 min; Test solution: 1 mg/mL, Solvent: Acetonitrile:methanol (1:1); Column flow: 1.5 ml/min.

Example 2. Preparation of Compound of Formula (I) in Toluene

Toluene 50 mL, 5.2 g of lauric anhydride (13.6 mmol), 5.0 g of compound of formula (II) obtained in step 1 (10.5 mmol) and 0.26 g 4-dimethylaminopyridine (2.1 mmol) were charged into a 250 mL reactor and kept under stirring at room temperature (15-25° C.) for a minimum of 4 hours (until compound of formula (II) in the reaction mixture was ≤ 0.5%). Results: 0% of unreacted starting material compound of formula (II), 10.0% of aripiprazole and 86.0% of aripiprazole lauroxil.

45 mL of toluene are distilled under reduced pressure (80° C., 600-700 mbar). 5 mL of solvent was left in the reaction. Then, 110 mL of isopropanol were charged and 90 mL of solvent were distilled at reduced pressure.

The reaction mixture was cooled to 0-10° C. It was kept 2 hours at 0-10° C. The mixture was filtered and the solid was washed twice with isopropanol (5 mL). The solid was dried under vacuum at 40° C. for 4 hours to obtain 5.6 g of aripiprazole lauroxil of 95.3% purity (analysed by HPLC) (82% yield).

Example 3. Preparation of Compound of Formula (I) in Tetrahydrofuran 40 mL of anhydrous THF, 3.5 g of lauric anhydride (9.2 mmol), 4.0 g of compound of formula (II) obtained in step 1 (8.4 mmol) and 0.20 g 4-dimethylaminopyridine (1.7 mmol) were charged into a 250 mL reactor and kept under stirring at room temperature (15-25° C.) for a minimum of 5 hours (until compound of formula (II) in the reaction mixture was ≤ 0.5%). Results: 0% of unreacted compound of formula (II), 10.0% of aripiprazole and 85.6% of aripiprazole lauroxil.

Comparative Example 2. Preparation of Aripiprazole Lauroxil from Compound of Formula (II) and Lauric Anhydride According to U.S. Pat. No. 8,431,576

30 mL of anhydrous THF, 5.0 g of compound of formula (II) obtained in step 1 of example 1 (10.45 mmol), 6.08 g of lauric anhydride (15.89 mmol) and 0.137 g of trimethylamine (1.36 mmol) were charged into a 100 mL reactor and kept under stirring for 16 hours. It was performed an HPLC analysis on the reaction mixture. Results: 32.8% of unreacted starting material compound of formula (II), 35.3% of aripiprazole and 26.7% aripiprazole lauroxil.

The invention claimed is:

1. A process for the preparation of a compound of formula (I)

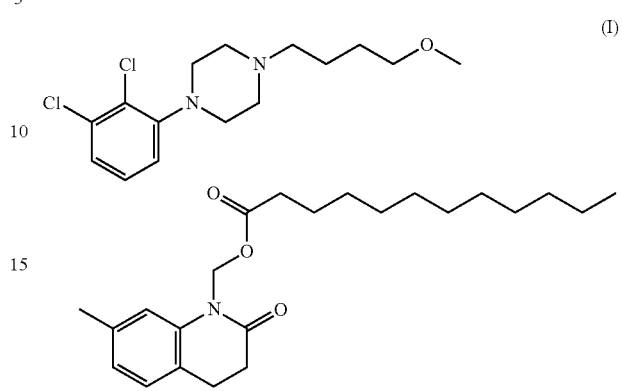

which is aripiprazole lauroxil, which comprises the following steps:
reacting a compound of formula (II)

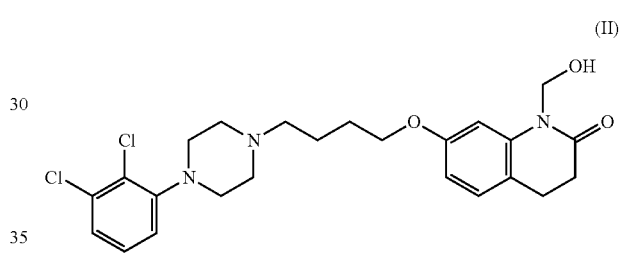

with lauric anhydride in the presence of DMAP and a solvent, to obtain aripiprazole lauroxil; and
optionally isolating the obtained compound of formula (I).

2. The process according to claim 1, wherein the solvent is selected from the group of dichloromethane, toluene, dimethylsulfoxide, dimethylformamide, dimethylacetamide, tetrahydrofuran, acetone, methyl ethyl ketone, methyl isobutyl ketone, acetonitrile, and mixtures thereof.

3. The process according to claim 2, wherein the solvent is dichloromethane.

4. The process according to claim 1, wherein the reaction temperature is in the range of room temperature and the boiling point of the solvent.

5. The process according to claim 4, wherein the reaction is performed at room temperature.

6. The process according to claim 1, wherein the amount of DMAP used is 0.2 to 0.3% molar with respect to the compound of formula (II).

7. The process according to claim 1, wherein the molar ratio of the compound of formula (II) to lauric anhydride is 1:1.3.

8. The process according to claim 3, wherein optionally isolating the obtained compound of formula (I) is carried out by distilling the solvent at atmospheric pressure.

9. The process according to claim 1, further comprising, before the step of reacting the compound of formula (II), a step of preparing the compound of formula (II)

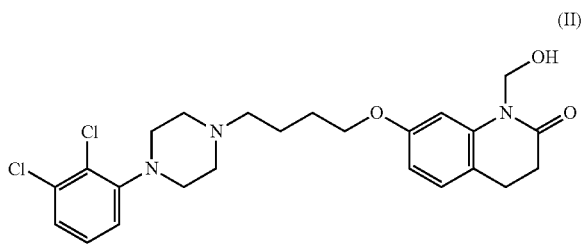 [SMILES: O=C1CCc2ccc(OCCCCN3CCN(c4cccc(Cl)c4Cl)CC3)cc2N1CO]

by reacting a compound of formula (III)

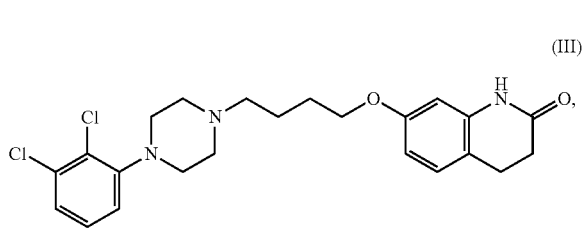 [SMILES: O=C1CCc2ccc(OCCCCN3CCN(c4cccc(Cl)c4Cl)CC3)cc2N1]

which is aripiprazole or a hydrate thereof, with paraformaldehyde in the presence of an organic solvent and a suitable base,
wherein the process is carried out either in the absence of water or in the presence of a content of water which comes from either the use of a non-anhydrous organic solvent, non-anhydrous reactants, or the use of a hydrated form of aripiprazole, without addition of further water.

10. The process according to claim 9, wherein the organic solvent is selected from the group of toluene, ethyl acetate, dimethylsulfoxide, dimethylformamide, dimethylacetamide, tetrahydrofuran, acetone, methyl ethyl ketone, methyl isobutyl ketone, dichloromethane, acetonitrile, and mixtures thereof.

11. The process according to claim 9, wherein the base is selected from the group of 1,8-diazabicyclo[5.4.0]undec-7-ene, 1,4-diazabicyclo[2.2.2]octane, potassium carbonate, sodium carbonate, cesium carbonate, potassium tert-butoxide, and diisopropylethylamine.

12. The process according to claim 9, wherein the amount of water in the reaction mixture comprising aripiprazole and paraformaldehyde is equal to or lower than 1 wt %.

13. The process according to claim 9, wherein aripiprazole or a hydrate thereof, and paraformaldehyde are in a molar ratio of from 1:1 to 1:3.

14. The process according to claim 2, wherein the reaction temperature is in the range of room temperature and the boiling point of the solvent.

15. The process according to claim 2, wherein the amount of DMAP used is 0.2 to 0.3% molar with respect to the compound of formula (II).

16. The process according to claim 2, wherein the molar ratio of compound of formula (II) to lauric anhydride is 1:1.3.

17. The process according to claim 2, further comprising, before the step of reacting the compound of formula (II), a step of preparing the compound of formula (II)

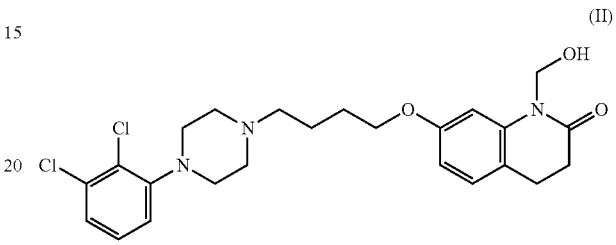

by reacting a compound of formula (III)

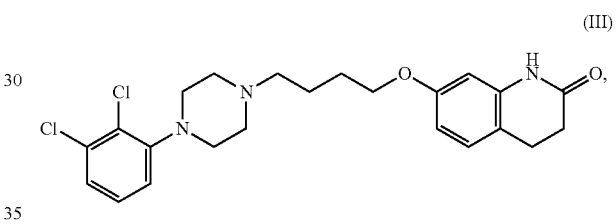

which is aripiprazole or a hydrate thereof, with paraformaldehyde in the presence of a organic solvent and a suitable base,
wherein the process is carried out either in the absence of water or in the presence of a content of water which comes from either the use of a non-anhydrous organic solvent, non-anhydrous reactants, or the use of a hydrated form of aripiprazole, without addition of further water.

18. The process according to claim 4, wherein the reaction temperature is in the range of 15-25° C.

19. The process according to claim 14, wherein the reaction temperature is in the range of 15-25° C.

* * * * *